United States Patent
Hohla

[11] Patent Number: 6,059,774
[45] Date of Patent: *May 9, 2000

[54] APPARATUS AND METHOD OF UNIFORMLY ABLATING A LAYER FROM THE SURFACE OF A SUBSTRATE

[75] Inventor: Kristian Hohla, Vaterstetten, Germany

[73] Assignee: Chiron Technolas GmbH Ophthalmologische Systeme, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/909,397

[22] Filed: Aug. 11, 1997

Related U.S. Application Data

[63] Continuation of application No. 08/480,129, Jun. 7, 1995, abandoned.

[30] Foreign Application Priority Data

Jan. 25, 1995 [DE] Germany ................... 195 02 258

[51] Int. Cl.[7] ..................................... A61N 5/06
[52] U.S. Cl. ..................... 606/5; 606/3; 606/10
[58] Field of Search ............ 606/2, 3–10, 13–18

[56] References Cited

U.S. PATENT DOCUMENTS

| | | |
|---|---|---|
| 4,665,913 | 5/1987 | L'Esperance, Jr. . |
| 4,669,466 | 6/1987 | L'Esperance . |
| 4,695,163 | 9/1987 | Schachar . |
| 4,718,418 | 1/1988 | L'Esperance, Jr. . |
| 4,729,372 | 3/1988 | L'Esperance, Jr. . |
| 4,732,148 | 3/1988 | L'Esperance, Jr. . |
| 4,770,172 | 9/1988 | L'Esperance, Jr. . |
| 4,773,414 | 9/1988 | L'Esperance, Jr. . |
| 4,784,135 | 11/1988 | Blum et al. . |
| 4,788,975 | 12/1988 | Shturman et al. . |
| 4,798,204 | 1/1989 | L'Esperance, Jr. . |
| 4,911,711 | 3/1990 | Telfair et al. . |
| 4,941,093 | 7/1990 | Marshall et al. . |
| 4,953,969 | 9/1990 | Fedorov . |
| 4,973,330 | 11/1990 | Azema et al. . |
| 5,108,388 | 4/1992 | Trokel . |
| 5,152,759 | 10/1992 | Parel et al. ................ 606/18 |
| 5,350,374 | 9/1994 | Smith . |
| 5,376,086 | 12/1994 | Khoobehi et al. . |
| 5,425,727 | 6/1995 | Koziol . |

FOREIGN PATENT DOCUMENTS

| | | |
|---|---|---|
| 111 060 | 9/1983 | European Pat. Off. . |
| 151 869 | 11/1984 | European Pat. Off. . |
| 164 858 | 4/1985 | European Pat. Off. . |
| 191 688 | 1/1986 | European Pat. Off. . |
| 207 648 | 6/1986 | European Pat. Off. . |
| 224 322 | 9/1986 | European Pat. Off. . |
| 257 836 | 7/1987 | European Pat. Off. . |
| 280 414 | 1/1988 | European Pat. Off. . |
| 306 409 | 1/1988 | European Pat. Off. . |
| 257 836 | 3/1988 | European Pat. Off. . |
| 296 982 | 6/1988 | European Pat. Off. . |
| 299 836 | 6/1988 | European Pat. Off. . |
| 296 982 | 12/1988 | European Pat. Off. . |
| 326 760 | 12/1988 | European Pat. Off. . |
| 356 282 | 7/1989 | European Pat. Off. . |
| 346 116 | 12/1989 | European Pat. Off. . |

(List continued on next page.)

OTHER PUBLICATIONS

Trokel, et al., "Excimer Laser Surgery of the Cornea," Am. J. Ophthalmology 96:710–715, 1983.

*Primary Examiner*—David M. Shay
*Attorney, Agent, or Firm*—Akin, Gump, Strauss, Hauer & Feld, LLP

[57] ABSTRACT

The apparatus and the method of ablating matter from a substrate using a laser, an optical system, and a screen arranged within the beam path of the laser. A laser spot is formed which exhibits light and dark sections. By adjusting the screen before each laser pulse, the entire surface area of the laser spot is subjected to the same number of laser pulses.

13 Claims, 3 Drawing Sheets

FOREIGN PATENT DOCUMENTS

| | | |
|---|---|---|
| 412 789 | 8/1990 | European Pat. Off. . |
| 447 067 | 2/1991 | European Pat. Off. . |
| 417 952 | 3/1991 | European Pat. Off. . |
| 628 298 | 12/1994 | European Pat. Off. . |
| 2 655 837 | 6/1991 | France . |
| 1 954 802 | 10/1969 | Germany . |
| 2 257 484 | 11/1972 | Germany . |
| 4001434 | 8/1990 | Germany . |
| WO 91/08723 | 6/1991 | WIPO . |
| WO 92/01430 | 2/1992 | WIPO . |
| WO 93/08877 | 5/1993 | WIPO . |

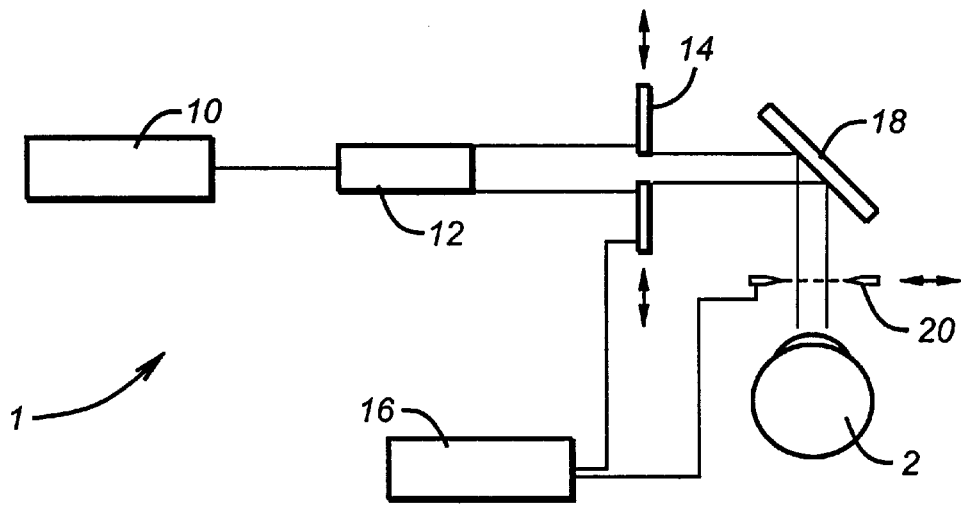
FIG. 4
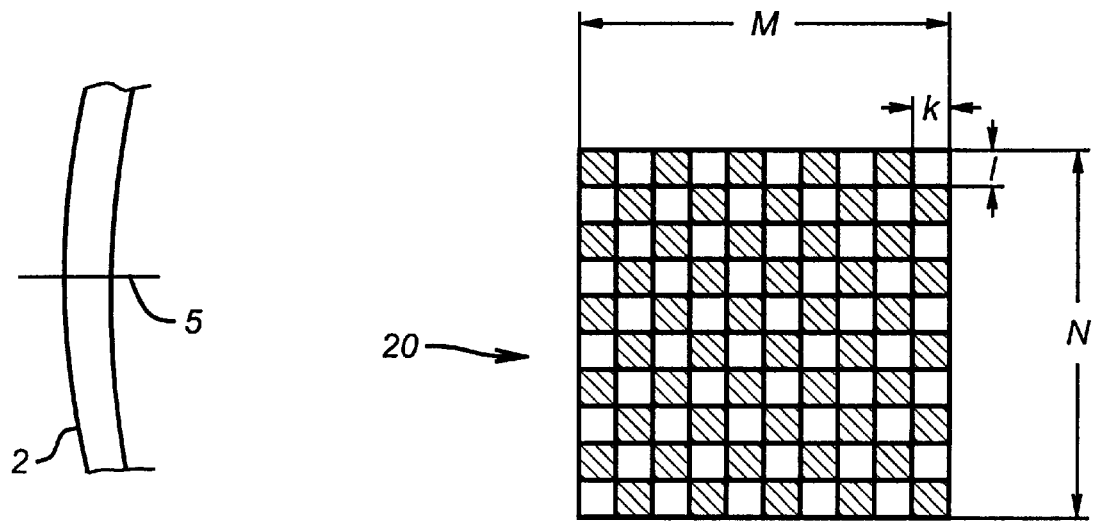
FIG. 5
FIG. 6

APPARATUS AND METHOD OF UNIFORMLY ABLATING A LAYER FROM THE SURFACE OF A SUBSTRATE

This is a continuation of application Ser. No. 08/480,129, filed on Jun. 7, 1995, now abandoned.

FOREIGN PRIORITY

This application claims priority under 35 U.S.C. §119 to German Patent Application No. 195-02-258.0 filed Jan. 25, 1995.

BACKGROUND OF THE INVENTION

1. Field of the Invention

The invention pertains to a method and apparatus for uniformly ablating a substrate, and more specifically, for performing photo refractive keratectomy on the eye.

2. Description of the Related Art

It is known to ablate tissue by means of laser beams for sculpting the cornea (photo-ablation). For this purpose, excimer lasers are preferably used whose wavelength are about 200 nm or more. FIG. 1 shows a known arrangement in which a laser beam of an excimer laser 10 is directed through a beam homogenizer 12 and an iris diaphragm 14 and subsequently by a mirror 18 onto the cornea of an eye 2. The size of the iris diaphragm is adjustable by means of a control device 16. Thus, the size of the spot formed on the cornea by the laser beam can be adjusted. By varying the surface area and shape of the spot and the number of laser pulses for certain sections of the surface of the cornea, the form of the cornea can be modified and an ametropia of the eye can be corrected.

FIG. 2, for example, shows how the shape of the cornea, which originally has a radius $R_1$, is flattened in a circular area having a diameter D by a laser treatment in such a way that subsequently an effective radius $R_2$ is achieved. In the area of the optical axis 5 of the eye 2, the ablated layer has a thickness A.

For reasons as yet unknown, the tissue is often not uniformly removed. That is, after a treatment with the known apparatus the shape of the cornea deviates from the desired shape. As schematically shown in FIG. 3, which is an enlarged view of the area marked with a circle in FIG. 2, less tissue is excised in the area of the optical axis than at the edge. Experiments have resulted in a deviation x in the order of magnitude of 5 to 10 $\mu$m, measured in an area having a diameter d of 2 to 3 mm and being symmetrical to the optical axis 5. This so-called "central island" problem has so far been obviated by pre-and after-treating the central area in such a way that this elevation has been ablated by means of laser pulses while correspondingly varying the adjustment of the iris diaphragm 14. However, the results of such an after treatment are often dissatisfying.

The uniform elimination of central islands from a treated area would therefore be greatly desirable.

SUMMARY OF THE INVENTION

The invention is based on the idea of dividing the laser spot generated by conventional apparatus into several exposed and unexposed sections. Thus, each laser pulse excises tissue only in the exposed section. By readjusting the apparatus, sections which have not been exposed are exposed during the following laser pulse and tissue is removed to the effect that tissue is uniformly excised from the entire surface area of the laser spot. In contrast to the prior art, the ablation with respect to the predetermined size of the laser spot is not effected in one step but in several steps. The advantage of this method is that a uniform area is ablated and that the aforementioned "central island" problem is circumvented. Preferably, the exposed sections have such a size and shape that the distance of each point within an exposed section to the next unexposed point, i.e., outside the section, is less than 1.5 mm. If the exposed section is circular, this circle preferably has a radius of less than 1.5 mm.

The ratio of the surface area of the exposed sections to that of the unexposed sections is preferably between 1:5 to 5:1. The exposed and the unexposed sections can be distributed regularly or irregularly within the laser spot. In the central zone of the laser spot, the proportion of the exposed sections can, for example, be higher than in an outer zone.

A screen diaphragm is preferably arranged within the beam path in the area in front of the surface area to be treated. Alternatively, the screen diaphragm can be arranged between the laser and the beam homogenizer, between the homogenizer and the iris diaphragm, or between the iris diaphragm and the tilted mirror. As an alternative to a reciprocating movement in one direction, the screen diaphragm can be moved in several directions, e.g., along the line of a rectangle, a polygon, or a circle in a plane, and essentially perpendicularly to the axis of the laser beam. In addition to or instead of this movement, the screen diaphragm can be rotated around the axis of the laser beam or an axis parallel to the axis of the laser beam.

Instead of a screen diaphragm, a mask can be used which is provided with several sections that are transparent to the laser beam, and whose remaining sections are non-transparent to the laser beam. The advantage of a mask is that any pattern of transparent and non-transparent sections can be produced.

According to a further preferred embodiment of the invention, a mirror, certain sections of which are reflective, is arranged within the beam path. A tilted mirror arranged within the beam path can for example be used certain sections of which are reflective. According to the pattern of the reflective sections of the mirror, a laser spot with exposed and unexposed sections is produced on the surface area of the substrate to be treated. By adjusting the position of the mirror correspondingly and/or rotating the mirror around an adjustment axis before each laser pulse, different sections of the area to be treated can be exposed one after the other.

In a further developed embodiment of the invention, several means are arranged within the beam path. Several screen diaphragms and also combinations with masks or mirrors can be used. Two screen diaphragms of the same type that are shiftable with respect to each other can be arranged such that the size and shape of the exposed sections of the laser spot can be varied.

According to a preferred embodiment, a laser spot with a checkered pattern is produced by the means, i.e., the screen diaphragm, the mask, or the mirror, having a certain reflective pattern. The number of the exposed sections of the laser spot corresponds to that of the unexposed sections and both types of sections have the same size and are regularly distributed. Alternatively, bar patterns of adjacent exposed and unexposed stripes can be produced. The advantage of regular patterns is that the means are adjusted according to a given pattern prior to each laser pulse or a series of laser pulses. However, any pattern, optionally even with exposed sections of different sizes and shapes, can be produced, preferably by adjusting the means such that statistically a uniform removal of tissue is achieved on the surface of the substrate to be treated.

BRIEF DESCRIPTION OF THE DRAWINGS

A better understanding of the present invention can be obtained when the following detailed description of the preferred embodiment is considered in conjunction with the following drawings, in which:

FIG. 4 shows a preferred embodiment of an apparatus according to the invention;

FIG. 5 shows a view of a zone of the cornea corresponding to that of FIG. 3 after a treatment with the apparatus of the invention according to FIG. 4;

FIG. 6 shows a screen diaphragm having a checkered pattern;

DETAILED DESCRIPTION OF THE PREFERRED EMBODIMENT

Figure 1:
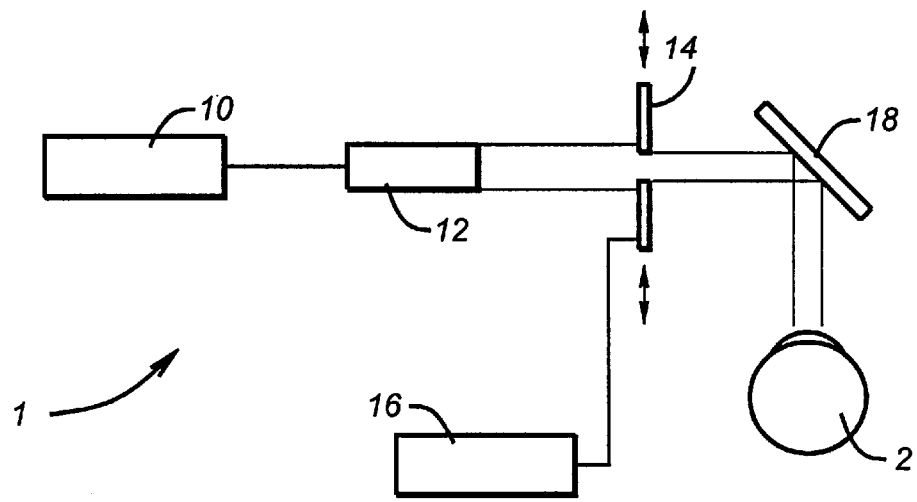
FIG. 1 shows a known apparatus for sculpting a cornea by ablating tissue by means of laser pulses.
Figure 2:
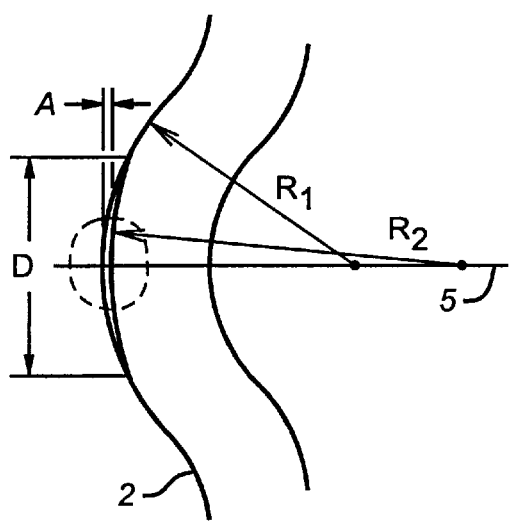
FIG. 2 shows a schematic view of the cornea prior to and after the treatment.

Turning now to the drawings, FIG. 4 largely corresponds to the apparatus depicted in FIG. 1, described above. Additionally, a screen diaphragm 20 is positioned within the beam path of the laser between the mirror 18 and the eye 2. The screen diaphragm 20 can be reciprocated essentially transversely with respect to the axis of the laser beam. The movement of the screen diaphragm 20 is controlled by the control device 16. The control is preferably effected automatically by a computer as a function of the number of laser pulses. Moreover, the control device can also control the iris diaphragm 16.

The screen diaphragm forms a laser spot having a light/dark pattern on the surface to be treated. In contrast to the prior art, the spot not only consists of a light area, but part of this area is shaded such that a multitude of small exposed sections are formed with adjacent, unexposed sections. Preferably, the screen diaphragm is repositioned before each laser pulse and then preferably those sections on the surface area to be treated are exposed which have not been exposed before. After a desired series of adjustments, the entire surface area to be treated is exposed. As a result, the ablated layer of tissue exhibits a uniform thickness.

Figure 3:
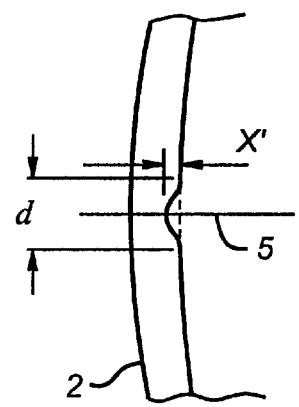
FIG. 3 shows a partial view of the section of FIG. 2 which is marked with a circle in more detail.

The screen diaphragm according to the invention can advantageously be used in a laser treatment for sculpting the cornea. Thus, a uniform ablation over entire surface area to be treated can be achieved. As evident from FIG. 5, this treatment prevents an elevation ("central island") around the optical axis 5, as depicted in FIG. 3. The advantage is that a pre- or after-treatment, which has so far frequently been necessary, can be avoided and a uniform surface structure can be achieved.

According to one embodiment, a screen diaphragm 20 exhibiting a checkered pattern can be used, as shown in FIG. 6. The checkered pattern has a width M and a height N and consists of exposed and unexposed sections which are regularly distributed and have a width k and a height l. In the depicted embodiment, the screen diaphragm as well as the individual exposed and unexposed sections are square. Such a screen diaphragm 20 is reciprocated by the control device 16 by the unit k, l in one direction. Thus, after two laser pulses, the entire surface area to be treated is exposed.

According to the present invention, any means can be used which divides the laser spot into exposed (light) and unexposed (dark) sections. The surface area covered by the exposed sections can on the whole correspond to that covered by the unexposed sections, as, for example, in the checkered screen diaphragm according to FIG. 6. According to the invention, the surface area covered by the exposed sections can be smaller or larger than that covered by the unexposed sections. The ratio of exposed to unexposed sections is preferably between 1:5 to 5:1. Using a ratio other than 1:1, the screen diaphragm is repositioned several times for total coverage. If, for example, a screen diaphragm is used which has two unexposed sections adjacent to one exposed section and having the same size, the screen diaphragm must be shifted three times on the whole prior to each laser pulse for exposing the entire surface area to be treated to effect a treatment equivalent to one laser pulse when the screen is not used.

Preferably, the pattern of the screen diaphragm is regular. Alternatively, screen diaphragms can be used which have different ratios of exposed to unexposed sections over the surface area of the screen diaphragm. A screen diaphragm can, for example, be used which has in certain zones, such as in the center or at the edge, a higher proportion of light or dark sections.

Figure 7:
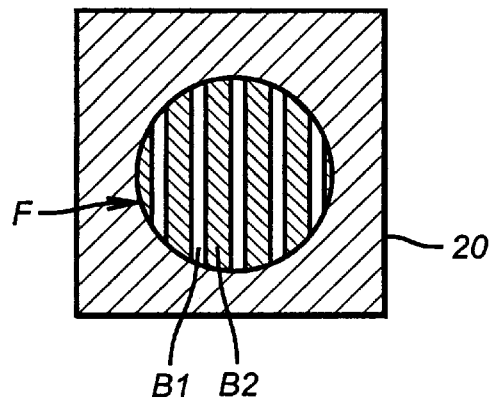
FIG. 7 shows a laser spot with a bar-like pattern.
Figure 8:
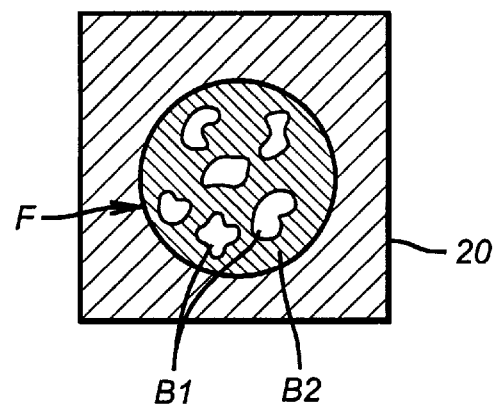
FIG. 8 shows a mask with several exposed sections.
Figure 9:
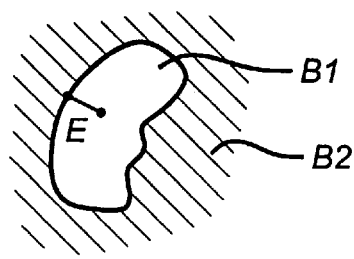
FIG. 9 shows a partial view of the mask depicted in FIG. 8.

FIG. 7 shows a laser spot which exhibits bar-shaped exposed and unexposed sections parallel to each other. FIG. 8 depicts a mask having exposed sections of different shapes and sizes. From FIG. 9, which depicts a partial view of FIG. 8, it is evident that the shape and size of each exposed section has preferably been selected such that the distance between any point within the exposed section and the edge of the exposed section, i.e., an unexposed point E, is less than 1.5 mm. Thus, in the case of the laser spot depicted in FIG. 7, the exposed stripes have preferably a width of less than 3 mm. The length of the stripes is arbitrarily chosen. In the screen diaphragm according to FIG. 6, the width k and the height l of the exposed sections are less than 3 mm each.

The present invention can in particular be advantageously used in a method for sculpting the cornea of an eye, wherein in particular by means of an adjustable iris diaphragm a laser spot of varying size and shape can be formed on the cornea. The invention can, however, also be used in other technical fields, i.e., for removing matter from any substrate.

The foregoing disclosure and description of the invention are illustrative and explanatory thereof, and various changes in the size, shape, materials, components, circuit elements, wiring connections and contacts, as well as in the details of the illustrated circuitry and construction and method of operation may be made without departing from the spirit of the invention.

What is claimed is:

1. An apparatus for ablating matter from a substrate comprising:

a laser emitting a laser beam having a beam path and of a suitable wavelength;

an optical system coupled to the laser and directing said laser to form a laser spot on a surface area of the substrate to be treated, and said optical system directing the laser beam in a pattern to create a vision correcting ablation profile suitable for reprofiling the surface of a cornea through volumetric removal yielding altered refractive characteristics; and a mask independent of the optical system arranged within the beam path of the laser for shading part of the substrate such that a plurality of exposed and unexposed sections are simultaneously formed on the substrate to be treated, wherein the mask is successively readjusted so that a sum of ablations yields an ablation profile that is proportional to the vision correcting ablation profile, and wherein the exposed and unexposed sections are distributed over the substrate to be treated such that the amount of laser light falling on a substrate over the sum of ablations is dependent on the optical system rather than the mask.

2. The apparatus of claim 1, wherein each of the exposed sections is of such a size or shape that the distance of each exposed point within this section to the next unexposed point outside this section is less than 1.5 mm.

3. The apparatus of claim 1, wherein the ratio of the areas of the exposed sections to the unexposed sections on the substrate is between 1:5 and 5:1.

4. The apparatus of claim 1, wherein the sizes and/or shapes of the exposed and/or unexposed sections are identical.

5. The apparatus of claim 1, wherein the mask is adjustable essentially perpendicularly to an axis of the laser beam in at least one direction.

6. The apparatus of claim 1, wherein the mask is rotatable essentially around the axis of the laser beam or an axis which is parallel to the axis of the laser beam.

7. The apparatus of claim 1, wherein the mask comprises at least one screen.

8. The apparatus of claim 1, wherein the mask comprises a mirror which is reflective in certain sections.

9. The apparatus of claim 1, wherein the mask has a checkered pattern.

10. The apparatus of claim 1, wherein the vision correcting ablation profile comprises a vision correcting ablation profile for myopia.

11. The apparatus of claim 1, wherein the ablation profile that is proportional to the vision correcting ablation profile comprises an ablation profile for myopia that is proportional to a vision correcting profile for myopia.

12. The apparatus of claim 1, wherein said laser is an excimer laser, and wherein said optical system further comprises a homogenizer, an iris diaphragm, and a tilted mirror arranged in the path of the laser beam and wherein said optical system further comprises a control device by means of which the opening of the iris diaphragm can be changed.

13. The apparatus of claim 12, wherein the iris diaphragm is adapted to create a vision correcting profile for myopia.

* * * * *